(12) United States Patent
Rhers et al.

(10) Patent No.: US 11,124,627 B2
(45) Date of Patent: Sep. 21, 2021

(54) PLASTICIZING COMPOSITION

(71) Applicant: Performance Polyamides, SAS, Paris (FR)

(72) Inventors: Bouchra Rhers, Mistral (FR); Daniel Martinz, Woluwe-Saint-Lambert (BE)

(73) Assignee: Performance Polyamides, SAS, Lyons (FR)

( * ) Notice: Subject to any disclaimer, the term of this patent is extended or adjusted under 35 U.S.C. 154(b) by 123 days.

(21) Appl. No.: 16/042,932

(22) Filed: Jul. 23, 2018

(65) Prior Publication Data

US 2019/0016873 A1    Jan. 17, 2019

Related U.S. Application Data

(62) Division of application No. 14/783,702, filed as application No. PCT/EP2014/057071 on Apr. 8, 2014, now abandoned.

(30) Foreign Application Priority Data

Apr. 10, 2013 (FR) ........................................ 1353227
Jun. 19, 2013 (EP) ...................................... 13172646

(51) Int. Cl.
| | | |
|---|---|---|
| *C08K 5/11* | (2006.01) | |
| *C09D 127/06* | (2006.01) | |
| *C08K 5/10* | (2006.01) | |
| *C07C 67/08* | (2006.01) | |
| *C08J 9/00* | (2006.01) | |
| *C08K 5/101* | (2006.01) | |
| *C08K 5/12* | (2006.01) | |
| *C09D 11/00* | (2014.01) | |
| *C09J 127/06* | (2006.01) | |

(52) U.S. Cl.
CPC ................ *C08K 5/11* (2013.01); *C07C 67/08* (2013.01); *C08J 9/00* (2013.01); *C08K 5/10* (2013.01); *C08K 5/101* (2013.01); *C08K 5/12* (2013.01); *C09D 11/00* (2013.01); *C09D 127/06* (2013.01); *C09J 127/06* (2013.01); *C07C 2601/14* (2017.05); *C08J 2327/06* (2013.01)

(58) Field of Classification Search
CPC . C08K 5/11; C08K 5/10; C08K 5/101; C08K 5/12; C07C 67/08; C08J 2327/06; C09J 127/06
See application file for complete search history.

(56) References Cited

U.S. PATENT DOCUMENTS

| | | | | |
|---|---|---|---|---|
| 3,632,467 A | * | 1/1972 | Todd .................. | C08G 59/5086 428/215 |
| 2009/0224204 A1 | * | 9/2009 | Marion ................... | C07C 67/22 252/364 |
| 2011/0196081 A1 | | 8/2011 | Kwon et al. | |

FOREIGN PATENT DOCUMENTS

| | | |
|---|---|---|
| CN | 101152582 A | 4/2008 |
| DE | 19938159 A1 | 2/2001 |
| EP | 13167 A1 | 7/1980 |
| EP | 13506 A2 | 7/1980 |
| EP | 1454958 A1 | 9/2004 |
| EP | 1491523 A1 | 12/2004 |
| FR | 1488857 A | 7/1967 |
| FR | 2400058 A1 | 3/1979 |
| FR | 2898356 A1 | 9/2007 |
| JP | S5590541 A | 7/1980 |
| JP | S55123634 A | 9/1980 |
| JP | H7149924 A | 6/1995 |
| JP | H7278387 A | 10/1995 |
| JP | 2009529025 A | 8/2009 |
| WO | 2007/101929 A1 | 9/2007 |
| WO | 2007/141404 A1 | 12/2007 |
| WO | 2008/062058 A1 | 5/2008 |
| WO | 2010030085 A2 | 3/2010 |

OTHER PUBLICATIONS

European Search Report dated Feb. 26, 2014, issued by the European Patent Office in corresponding European Application No. 13172646.5 (8 pages).
International Search Report dated Nov. 3, 2014, issued by the European Patent Office in corresponding International Application No. PCT/EP2014/057071 (2 pages).
Search report issued in Brazil Application No. BR112015024991-4, dated Dec. 5, 2019 (4 pages).
Office Action issued in corresponding European Application No. 14715638.4; dated Nov. 11, 2020 (11 pages).
Notice of Allowance issued in corresponding Korean Application No. 10-2015-7031791; dated Nov. 26, 2020 (4 pages).

* cited by examiner

*Primary Examiner* — Kara B Boyle

(74) *Attorney, Agent, or Firm* — Osha Bergman Watanabe & Burton LLP

(57) ABSTRACT

The invention relates to a plasticizing composition comprising a vinyl chloride resin and a plasticizing agent which comprises at least one diester having the general formula (I), derived from a diacid selected from succinic acid, glutaric acid, adipic acid, ethylsuccinic acid, methylglutaric acid and mixtures thereof wherein: A is a $C_4$ to $C_6$ linear or branched aliphatic chain, and R is an alkyl, a cycloalkyl or an aryl. The plasticizing agent according to the present invention has a good performance for different types of formulations (foam, film and paste). Said plasticizer gels rapidly, has a very low viscosity, and ages very well. Efficient debubblizing is one of the key properties thereof. The foams prepared with said plasticizer have very low densities, a high expansion rate, and excellent qualities.

4 Claims, 2 Drawing Sheets

PLASTICIZING COMPOSITION

CROSS-REFERENCE TO RELATED APPLICATIONS

The present application is a divisional filed pursuant to 35 U.S.C. § 121 of U.S. patent application Ser. No. 14/783,702, filed on Oct. 9, 2015, which is a U.S. National Entry Stage of International Application No. PCT/EP2014/057071, filed on Apr. 8, 2014 which claims priority to EP 13172646.5, filed on Jun. 19, 2013, and FR 1353227, filed on Apr. 10, 2013, the whole content of each of these applications being herein incorporated by reference for all purpose.

BACKGROUND

The invention relates to a plasticizing composition comprising a resin of vinyl chloride type and a plasticizing agent which comprises at least one diester derived from a diacid chosen from succinic acid, glutaric acid, adipic acid, ethylsuccinic acid, methylglutaric acid and their mixture. The present invention relates more particularly to a plasticizing agent which comprises at least one diester derived from a diacid chosen from succinic acid, glutaric acid, adipic acid, ethylsuccinic acid, methylglutaric acid and their mixture and to its process of preparation. The present invention also relates to the uses of the plasticizing composition.

PRIOR ART

The plasticizing agents predominantly used are commonly known as "General Purpose" (GP) phthalates and thus represent 88% of consumption worldwide (6.7 MTon in 2011). The GP phthalates family includes DEHP (di(2-ethylhexyl) phthalate), DINP (diisononyl phthalate) and DIDP (diisodecyl phthalate). These three combined phthalates represent of the order of 83% of worldwide demand for plasticizers. DEHP alone represents approximately 50% of worldwide demand.

Aim of the Invention

The general aim of the invention is to provide novel plasticizing compositions.

The plasticizing agent according to the invention exhibits a good performance for formulations of different types (foam, film and paste). This plasticizer rapidly gels, has a very low viscosity and ages very well. Efficient debubbling is one of these leading characteristics. The foams prepared with this plasticizer have low densities, a high rate of expansion and excellent qualities.

It is an aim in particular of the invention to provide a process which makes it possible to obtain the plasticizing agent.

The inventors have developed a process for the preparation of diester compounds starting from dinitriles and/or diacids employing a hydrolysis reaction followed by an esterification stage. A decoloration and/or purification stage makes it possible to obtain a pure diester.

The invention relates more particularly still to a process for the preparation of branched diester compounds, such as the diester of 2-methylglutaric acid (also known as MGA) and the diester of 2-ethylsuccinic acid (also known as ESA).

The diester based on MGA alone or as a mixture with the diester based on ESA has a promising future in the milieu of the chemical industries. It is a plasticizer having plasticizing properties which can replace plasticizers based on phthalates and devoid of phthalates. It can be used as replacement for plasticizer, all alone or as a mixture with other plasticizers, for preparations/formulations of polyamides, of concrete, of polyesters, of polyurethanes, of vinyl chloride resins, of ethylene/vinyl acetate copolymers, of rubber, of mastics or of their mixtures.

The diester is obtained either from dinitriles, involving a diacid intermediate, or from diacid directly.

WO 2007/141404 provides for the preparation of diacid compounds by hydrolysis of dinitrile compounds in the presence of an excess of basic hydroxyl compounds, the carboxylate salt obtained subsequently being reacted with an inorganic acid in order to recover the diacid compound.

WO 2008/062058 provides for the preparation of diacid compounds by hydrolysis of dinitrile compounds in the presence of an excess of strong inorganic acid.

WO2007/101929 provides for the preparation of diester by hydrolysis of dinitriles by the acid route or by the basic route; the diacid intermediate is subsequently esterified in the presence of methanol in order to obtain the corresponding dimethyl ester.

Figure 1:
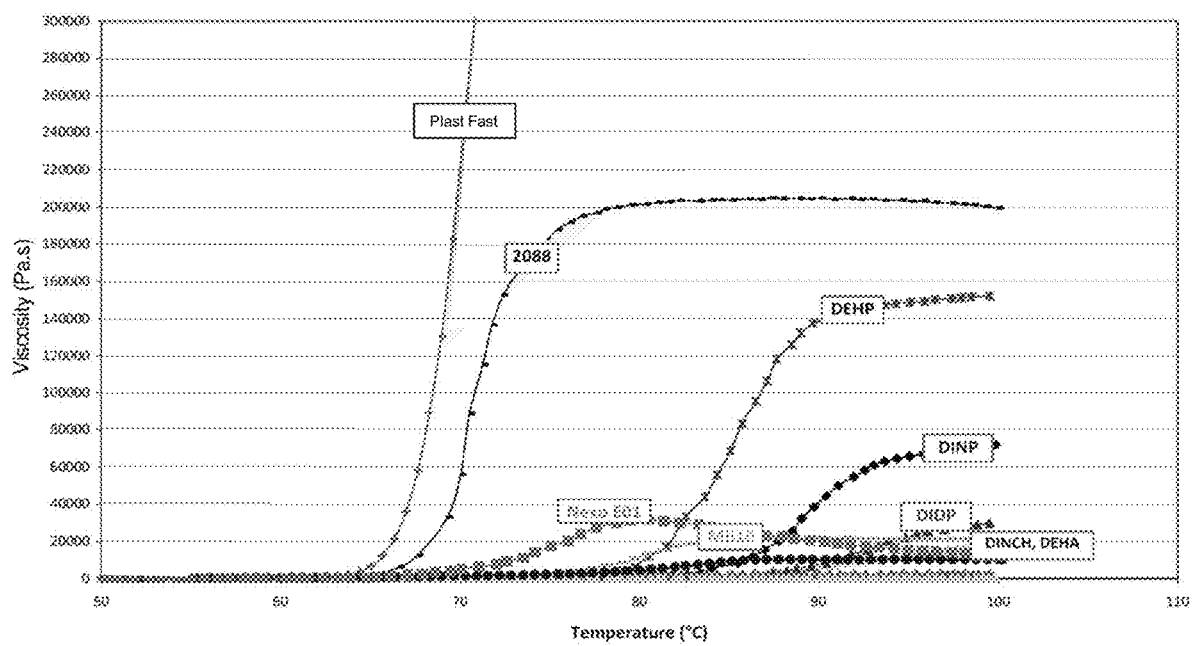
FIG. 1 depicts the gelation behavior of plasticizers (plate-plate rheology) according to the present embodiments.
Figures 2A, 2B, 2C:
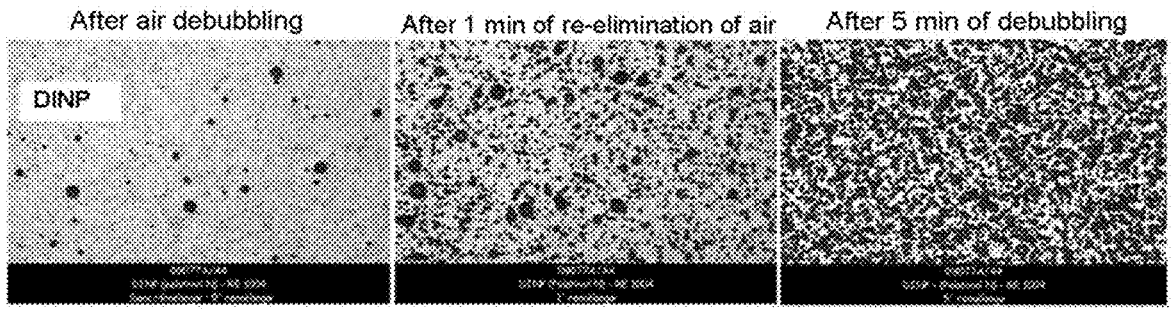
FIGS. 2A-2C, 3A-3C, 4A-4C, 5A-5C, 6A-6C show photographs depicting debubbling of various plasticizers according to the present embodiments.
Figures 3A, 3B, 3C:
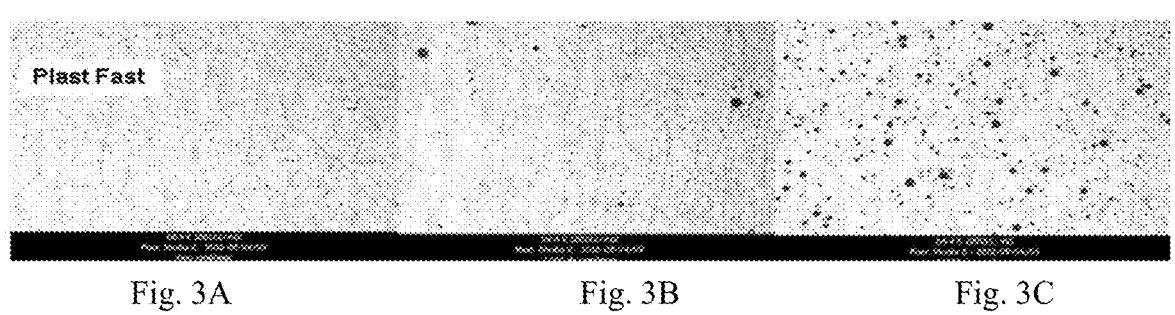
Figures 4A, 4B, 4C:
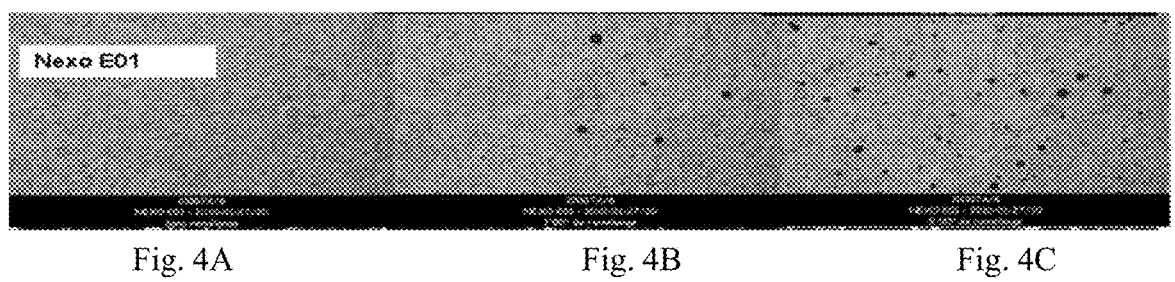
Figures 5A, 5B, 5C:
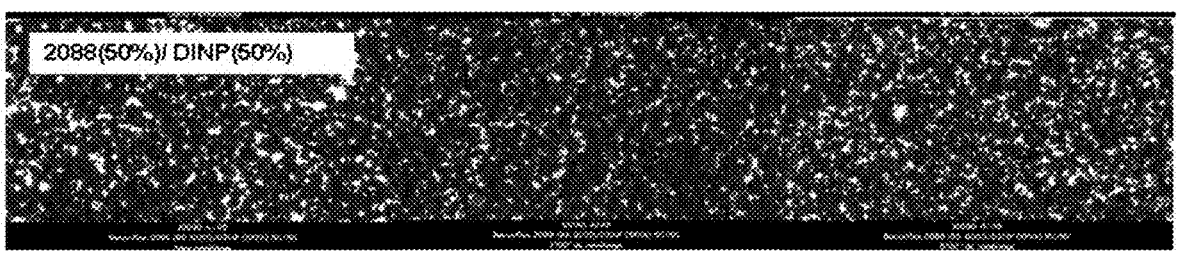
Figures 6A, 6B, 6C:
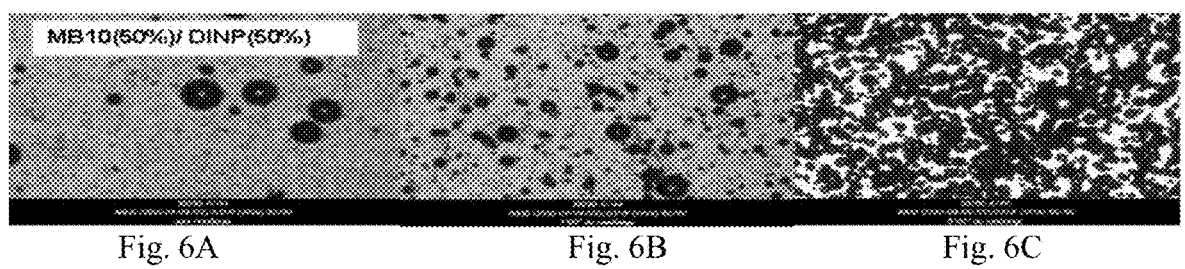

The present invention relates to a plasticizing composition comprising a resin and a plasticizing agent which comprises at least one diester of general formula (I):

derived from a diacid chosen from succinic acid, glutaric acid, adipic acid, ethylsuccinic acid, methylglutaric acid and their mixture, in which:
A can be a linear or branched aliphatic chain comprising from 4 to 6 carbons, and
R can be an alkyl, a cycloalkyl or an aryl;
in particular, R is a substituted or unsubstituted cycloalkyl of 5 to 6 carbon atoms;
or a branched alkyl having from 4 to 10 carbon atoms.
Preferably, R is cyclohexyl or 2-ethylhexyl.

According to one embodiment of the invention, the plasticizing agent comprises a mixture comprising:
from 70% to 95% by weight of methylglutaric acid diester;
from 5% to 30% by weight of ethylsuccinic acid diester;
from 0% to 10% by weight of adipic acid diester.

According to another embodiment of the invention, the plasticizing agent comprises a mixture comprising:
from 95% to 100% by weight of methylglutaric acid diester, and
from 0% to 5% by weight of ethylsuccinic acid diester.

According to a preferred embodiment of the invention, the diester is the dicyclohexyl one of methylglutaric acid (DCH-MGA).

According to another embodiment of the invention, the diester is the diethylhexyl one of adipic acid (DCH-AA).

According to a third embodiment of the invention, the diester is the diethylhexyl one of methylglutaric acid (DEH-MGA).

The plasticizer of this invention can be prepared by esterification of diacids with these cyclic alcohols.

Reactions:

During the hydrolysis reaction of the dinitrile compound in the presence of acid, diacids and ammonium hydrogensulfate salt are formed. The latter can be recovered in value in the form of ammonium sulfates by its reaction with another molecule of ammonia.

Diagrammatically, the hydrolysis reaction of a dinitrile compound, for example 2-methylglutaronitrile, to give a diacid intermediate compound of the process of the invention can be represented in the following way:

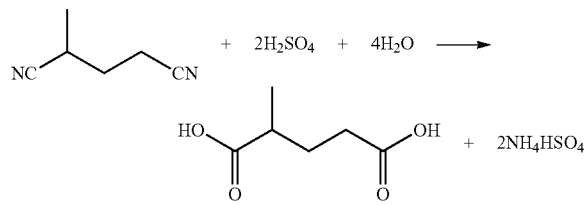

In the reaction medium, the diacid compound is subsequently subjected to an esterification reaction with an alcohol, for example cyclohexanol, to give a diester of the process of the invention in the following way:

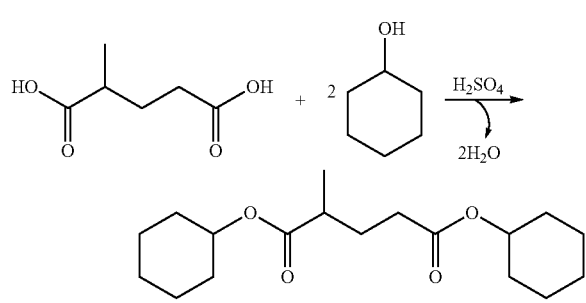

EXAMPLES

The percentages are given by weight, with respect to the weight of the total composition. The temperatures are given in degrees Celsius (° C.).

Example 1

General Procedure for the Synthesis of Plasticizers by Esterification.

The catalyst, for example sulfuric acid, is added at 80° C. to a 1000 ml jacketed reactor equipped with a system for bleeding at the bottom, with a stirring system, with a nitrogen inlet, with a thermometer, with a Dean and Stark apparatus, with a pump for providing the vacuum and with a dropping funnel equipped with a cooling and heating system, via which the acid and the alcohol, the stoichiometry of which is 1:2, are added. The reaction takes place at 140° C. with removal of the water as the reaction progresses. The stripping with nitrogen thus promotes its removal and its recovery in the Dean and Stark apparatus. Once the amount of water co-produced has been completely collected, the temperature is raised above 140° C. and the pressure is lowered in order to remove the excess alcohol. The reaction medium is subsequently washed several times with sodium chloride solutions and, at the end, with demineralized water. The remaining catalyst is neutralized with sodium carbonate. A stage of decoloration by passing through charcoal can be carried out according to the level of coloration of the medium. The organic phase comprising the diester is subsequently purified and decolored by distillation. The pure and colorless diester is thus obtained with good yields.

TABLE 1 summary of the diesters prepared by reaction of alcohol and diacids.

| Nomenclature | A | R | MW (g/mol) |
|---|---|---|---|
| Bis(2-ethylhexyl) succinate | —(CH$_2$)$_2$— | -2-Ethylhexyl | 342 |
| Bis(2-ethylhexyl) glutarate | —(CH$_2$)$_3$— | -2-Ethylhexyl | 356 |
| Dicyclohexyl adipate | —(CH$_2$)$_4$— | -Cyclohexyl | 310 |
| Bis(2-ethylhexyl) 2-methylglutarate | —CH$_2$—CH$_2$—CH(CH$_3$)— | -2-Ethylhexyl | 370 |
| Dicyclohexyl 2-methylglutarate | —CH$_2$—CH$_2$—CH(CH$_3$)— | -Cyclohexyl | 310 |
| Bis(2-ethylhexyl) 2-ethylsuccinate | —CH$_2$—CH(CH$_2$CH$_3$)— | -2-Ethylhexyl | 370 |
| Dicyclohexyl 2-ethylsuccinate | —CH$_2$—CH(CH$_2$CH$_3$)— | -Cyclohexyl | 310 |
| Plast Fast = mixture of 95% dicyclohexyl methylglutarate and 5% dicyclohexyl 2-ethylsuccinate | 95%: —CH$_2$—CH$_2$—CH(CH$_3$)— 5%: —CH$_2$—CH(CH$_2$CH$_3$)— | -Cyclohexyl | 310 |

Synthesis of Compounds Based on PVC: Plasticization

All the plasticizers used for the tests with the PVC resins under different formulations are summarized in table 2.

TABLE 2 description of the plasticizers

| Plasticizer | Manufacturer | Chemical name | MW (g/mol) |
|---|---|---|---|
| DEHP | Arkema | Di(2-ethylhexyl) phthalate | 390 |
| DINP | BASF | Diisononyl phthalate | 418 |
| DINCH | BASF | 1,2-Cyclohexanedicarboxylic acid, diisononyl ester | 425 |
| DOTP | Eastman | Di(2-ethylhexyl) terephthalate | 390 |
| Nexo E01 | Nexoleum | Methyl epoxy soyate | 327 |
| Benzoflex 2088 | Eastman | Mixture of benzoate esters (78-80%) and dipropylene glycol dibenzoate (18-20%) | 350 |
| Jayflex MB10 | Exxon | Isodecyl monobenzoate | 262 |
| Plast Fast | Solvay | 2-Methylglutarate diester | 310 |

A comparative assessment of the performances of the plasticizers studied was carried out for each formulation. The criteria for classifying the performance of the plasticizers, in comparison with DINP, are classified as follows:

| 0: idem | −0.5: slightly poorer | 0.5: slightly better |
|---|---|---|
| | −1: poorer | 1: better |
| | −2: bad | 2: excellent |
| | −3: very bad | 3: outstanding |

Example 2

Each plasticizer listed in table 2 makes it possible to produce transparent formulations according to table 3 below, using a mixer of medium-speed mixer type at a temperature of 23° C.

TABLE 3

Recipe for PVC pastes (compact transparent layers):

| Starting materials | Amount (phr) |
|---|---|
| SolVin ® 382NG | 100 |
| Plasticizer | 50 |
| Baerostab ® NT 306 (Ca/Zn) | 2.5 |

The comparison of the data obtained for the formulations synthesized, the plasticizer being modified on each occasion, are summarized in table 4.

TABLE 4

4a to 4i: evaluations and comparison of the properties

4a- Shore A: Hardness (on 6 mm plaques)

| Plasticizer | Curings in the oven (cutting) | Pressed films |
|---|---|---|
| DEHP | 67 | 75 |
| DINP | 72 | 78 |
| DINCH | 74.5 | 84 |
| DOTP | 71 | 76 |
| Nexo E01 | 66 | 70 |
| Plast Fast | 65 | 68 |
| MB10/DINP | 68 | 71 |
| 2088/DINP | 71 | 73 |

4b- Viscosity at low rate gradient (Eta = 1.4 s$^{-1}$)

| Plasticizer | t 0 | t 0 + 24 h |
|---|---|---|
| DEHP | 4.4 | 9.6 |
| DINP | 3.6 | 15.7 |
| DINCH | 2.0 | 3.4 |
| DOTP | 3.4 | 3.4 |
| Nexo E01 | 2.4 | 4.0 |
| Plast Fast | 2.7 | 5.9 |
| MB10/DINP | 1.6 | 36.0 |
| 2088/DINP | 14.4 | 13.4 |

4c- Relative gelation rate (ARES rheometer, plate-plate, 1 rad/s, temperatures from 23 to 100° C., rise of 3° C./min)

| Plasticizers | Gelation |
|---|---|
| DEHP | 0.75 |
| DINP | 0 |
| DINCH | −1.5 |
| DOTP | −0.75 |
| Nexo E01 | 1.25 |
| Plast Fast | 2.5 |
| MB10 | 1 |
| 2088 | 2 |

4d- Loss in weight (%) at 100° C. - ventilated oven

| Plasticizer | After 4 days | After 7 days |
|---|---|---|
| DEHP | 9.85 | 19.4 |
| DINP | 2.3 | 3.8 |
| DINCH | 6.3 | 10.2 |
| DOTP | 3.7 | 7.55 |
| Nexo E01 | 12.4 | 15.8 |
| Plast Fast | 20.7 | 24.6 |
| MB10/DINP | 16.4 | 17.6 |
| 2088/DINP | 4.7 | 6.9 |

4e- Color, gloss and transparency of the PVC films (0.7 mm, 190° C., 2 min)

| Plasticizer | Yellowness index | Gloss | Transparency |
|---|---|---|---|
| DEHP | 8.4 | 29.3 | 83.7 |
| DINP | 8.7 | 30.6 | 86.5 |
| DINCH | 8.1 | 35.5 | 85.35 |
| DOTP | 7.75 | 30.05 | 81.7 |
| Nexo E01 | 17.8 | 22.6 | 74.1 |
| Plast Fast | 11.4 | 29.1 | 87.9 |
| MB10/DINP | 8.0 | 23.2 | 82.6 |
| 2088/DINP | 9.3 | 25.8 | 82.4 |

4f- Debubbling

| Plasticizer | Column height (ml) | Time (s) |
|---|---|---|
| DEHP | 98 | 49.5 |
| DINP | 100.5 | 53 |
| DINCH | 100 | 60.5 |
| DOTP | 93 | 29 |
| Nexo E01 | 29 | 23 |
| Plast Fast | 94 | 37 |
| MB10/DINP | 83 | 22 |
| 2088/DINP | 100 | 100 |

4g- Thermal stability (DHC at 180° C. and Metrastat at 197° C.)

| Plasticizer | DHC (min) | Metrastat (min) |
|---|---|---|
| DEHP | 25 | 10 |
| DINP | 24.2 | 15 |
| DINCH | 28.3 | 11.6 |
| DOTP | 25.8 | 15.5 |
| Nexo E01 | 152 | 27 |
| Plast Fast | 27 | 19.15 |
| MB10/DINP | 25.8 | 19.3 |
| 2088/DINP | 30.6 | 18.5 |

4h- Compatibility plasticizer with PVC ASTM D3291-92

| Plasticizer | 0 | 1 Day | 1 Week | 2 Weeks | 4 Weeks | 8 Weeks |
|---|---|---|---|---|---|---|
| DINP | 0 | 0 | 0 | 0 | 0 | 0 |
| Plast Fast | 0 | 0 | 0 | 0 | 0 | 0 |

4i- Migration of the PVC film (0.7 mm, 190° C., 2 min)

| Plasticizer | Migration | Date of manufacture of the film | Comments |
|---|---|---|---|
| DEHP | 0 | September 2009 | dry sample |
| DINP | 0 | September 2009 | dry sample |
| DINCH | 0 | September 2009 | dry sample |
| DOTP | 0 | April 2010 | dry sample |
| Nexo E01 | −0.5 | April 2010 | presence of exudation on the paper |
| Plast Fast | 0 | November 2012 | dry sample |
| MB10/DINP | 0 | August 2010 | dry sample |
| 2088/DINP | 0 | August 2010 | dry sample |

The best performances which emerge for the "Plast Fast" plasticizer are the gelation and the debubbling. This phenomenon is illustrated in FIG. 1 and the photographs taken for the debubbling are presented in FIGS. 2A-2C, 3A-3C, 4A-4C, 5A-5C, 6A-6C. Referring to FIGS. 2A, 3A, 4A, 5A and 6A, FIGS. 2A, 3A, 4A, 5A and 6A are taken after air debubbling. In FIGS. 2B, 3B, 4B, 5B and 6B, it should be understood that the photographs are taken after 1 minute of resumption of the mixing (that is to say, reincorporation of air). The same applies for the photographs depicted in FIGS. 2C, 3C, 4C, 5C and 6C taken after 5 minutes of debubbling.

The classification of the plasticizers according to the grades assigned are summarized in table 5.

TABLE 5

Summary of the properties obtained with the plasticizers in the transparent PVC paste formulations

| Plasticizer | Viscosity | Aging | Gelation | Efficacy | Debubbling | Thermal stability | Color | Transp. | Gloss | Loss in weight | Migration | Score |
|---|---|---|---|---|---|---|---|---|---|---|---|---|
| DEHP | 0 | 0.5 | 0.75 | 1 | 0 | −0.125 | 0 | 0 | 0 | −2 | 0 | 0.125 |
| DINP | 0 | 0 | 0 | 0 | 0 | 0 | 0 | 0 | 0 | 0 | 0 | 0 |
| DINCH | 0.5 | 1.25 | −1.5 | −0.75 | 0 | 0 | 0 | 0 | 0.75 | −1 | 0 | −0.75 |
| DOTP | 0 | 1.25 | −0.75 | 0.25 | 0 | 0 | 0 | −0.5 | 0 | −0.75 | 0 | −0.5 |
| Nexo E01 | 0 | 1 | 1.25 | 1.375 | 1 | 3 | −1.5 | −0.75 | −0.5 | −1.5 | −0.5 | 2.875 |
| Plast Fast | 0.25 | 0.75 | 2.5 | 1.5 | 0.75 | 0.25 | −0.5 | 0 | 0 | −2.75 | 0 | 2.75 |
| MB10/DINP | 0.75 | −0.5 | 1 | 1.125 | −0.5 | 0.125 | 0 | −0.25 | −0.5 | −1.75 | 0 | −0.5 |
| 2088/DINP | −2 | 0 | 2 | 0.7 | −1.5 | 0.25 | −0.25 | −0.25 | −0.25 | −0.5 | 0 | −1.81 |

Example 3

Foam formulations corresponding to table 6 were produced with each plasticizer of table 2 in a mixer of medium-speed type.

TABLE 6

Recipe for PVC pastes - foam-type formulations (expanded layers):

| Starting materials | Amount (phr) |
|---|---|
| SolVin 367NK | 100 |
| Plasticizer | 62 |
| $CaCO_3$ (15 mm) | 40 |
| Porofor® ADC (50%) + DINP | 6 |
| Baerostab® KK42 (K/Zn) | 2.0 |

The comparison of the data obtained for the formulations synthesized, the plasticizer being modified on each occasion, are summarized in table 7.

TABLE 7

7a and 7b: evaluations and comparison of the properties

7a- Rheology and aging of the paste at low rate gradient (Eta = 1.4 $s^{-1}$)

| Plasticizer | t 0 | t 0 + 24 h |
|---|---|---|
| DEHP | 9.1 | 8.5 |
| DINP | 7.2 | 6.5 |
| DINCH | 7.4 | 5.6 |
| DOTP | 10.6 | 7.5 |
| Nexo E01 | 3.8 | 5.0 |
| Plast Fast | 11.4 | 11.7 |
| MB10/DINP | 2.1 | 2.5 |
| 2088/DINP | 6.9 | 7.3 |

TABLE 7-continued 7a and 7b: evaluations and comparison of the properties

7b- Density, color, rate of expansion, and cell quality (thickness 0.35 mm, 2 min at 200° C.)

| Plasticizer | Density (g/$cm^3$) | Rate of expansion | Yellowness index | Cell quality |
|---|---|---|---|---|
| DEHP | 0.25 | 5.1 | 12.9 | Very good |
| DINP | 0.25 | 5.27 | 14.19 | Very good |
| DINCH | 0.25 | 5.2 | 15.2 | Very good |
| DOTP | 0.26 | 5.2 | 11.25 | Very good |
| Nexo E01 | 0.24 | 5.6 | 47.7 | Moderate |
| Plast Fast | 0.21 | 6.3 | 19.4 | Good |
| MB10/DINP | 0.25 | 5.4 | 14 | Very good |
| 2088/DINP | 0.25 | 5.2 | 16.2 | Very good |

The classification of the plasticizers according to the grades assigned are summarized in table 8.

TABLE 8

Summary of the properties obtained with the plasticizers in the PVC foam formulations

| Plasticizer | Viscosity | Aging | Color | Density | Rate exp | Cell quality | Score |
|---|---|---|---|---|---|---|---|
| DEHP | −0.5 | 0 | 0.5 | 0 | 0 | 0 | 0 |
| DINP | 0 | 0 | 0 | 0 | 0 | 0 | 0 |
| DINCH | 0 | 0 | 0 | 0 | 0 | 0 | 0 |
| DOTP | −0.75 | 0 | 0.5 | 0 | 0 | 0 | −0.25 |
| Nexo E01 | 1 | 0 | −2.5 | 0.5 | 0.5 | −1 | −1.5 |
| Plast Fast | −0.75 | 0 | −0.75 | 1 | 1.25 | −0.5 | 0.25 |
| MB10/DINP | 1.5 | 0 | 0 | 0 | 0.25 | 0 | 1.75 |
| 2088/DINP | 0 | 0 | 0 | −0.25 | 0 | 0 | −0.25 |

The general comparison of these 2 formulations allows us to have the result of the overall performance of the plasticizers. The mean of the score of the transparent layers and the score of the foam layers gives us the overall performance score for each plasticizer and thus allows us to compare them. The total score of the performances evaluated is given in table 9.

TABLE 9

Total score of the performances of each plasticizer.

| Plasticizer | Score transparent layers | Score foam layers | Total score |
|---|---|---|---|
| DEHP | 0.125 | 0 | 0.125 |
| DINP | 0 | 0 | 0 |
| DINCH | −0.75 | 0 | −0.75 |
| DOTP | −0.5 | −0.25 | −0.75 |
| Nexo E01 | 2.875 | −1.5 | 1.38 |
| Plast Fast | 2.75 | 0.25 | 3 |
| MB10/DINP | −0.5 | 1.75 | 1.25 |
| 2088/DINP | −1.8125 | −0.25 | −2.06 |

On average, the Plast Fast exhibits a good performance for the 2 recipes tested; it has the highest score in comparison with the other plasticizers. This plasticizer rapidly gels, has a very low viscosity and ages very well. Efficient debubbling is one of these leading characteristics. The foams prepared with this plasticizer have low densities, a high rate of expansion and excellent qualities.

The invention claimed is:

1. A plastisol comprising:
 a vinyl chloride resin; and
 a plasticizing agent,
 wherein the plasticizing agent is a mixture of
  from 95% to 100% by weight of dicyclohexyl methylglutarate, and
  from 0% to 5% by weight of dicyclohexyl 2-ethylsuccinate, and
 wherein the plastisol is in the form of a paste, film, or foam.

2. The plastisol of claim 1, wherein the plastisol additionally comprises one or more compounds selected from stabilizers, fillers, pigments, biocides, carbon black, adhesion promoters, viscosity reducers, thixotropic agents, thickening agents, blowing agents, dispersants and other additives.

3. The plastisol of claim 1, wherein the plasticizing agent additionally comprises one or more compounds selected from phthalate, adipate, benzoate, triglyceride and other polymers.

4. The plastisol of claim 1, wherein the plastisol is an adhesive or an ink.

* * * * *